(12) United States Patent
Castor

(10) Patent No.: US 8,435,575 B2
(45) Date of Patent: May 7, 2013

(54) USE OF GINGEROLS FOR CANCER PATIENTS SUFFERING FROM NAUSEA AND EMESIS INDUCED BY CHEMOTHERAPY

(75) Inventor: Trevor Castor, Arlington, MA (US)

(73) Assignee: Aphios Corporation, Woburn, MA (US)

( * ) Notice: Subject to any disclaimer, the term of this patent is extended or adjusted under 35 U.S.C. 154(b) by 0 days.

(21) Appl. No.: 12/800,345

(22) Filed: May 13, 2010

(65) Prior Publication Data

US 2011/0280976 A1   Nov. 17, 2011

(51) Int. Cl.
*A61K 36/9068* (2006.01)

(52) U.S. Cl.
USPC .......................................... 424/756; 424/773

(58) Field of Classification Search ........................ None
See application file for complete search history.

(56) References Cited

U.S. PATENT DOCUMENTS

2007/0154575 A1* 7/2007 Shimoda et al. .............. 424/756

OTHER PUBLICATIONS

Bailey-Shaw (Journal of Agricultural and Food Chemistry (2008), vol. 56, pp. 5564-5571).*

* cited by examiner

*Primary Examiner* — Susan Hoffman
(74) *Attorney, Agent, or Firm* — Pearl Cohen Zedek Latzer, LLP

(57) ABSTRACT

This invention is for an improved method for making enhanced ginger capsules and for using these capsules for treating nausea and emesis in cancer patients.

9 Claims, 1 Drawing Sheet

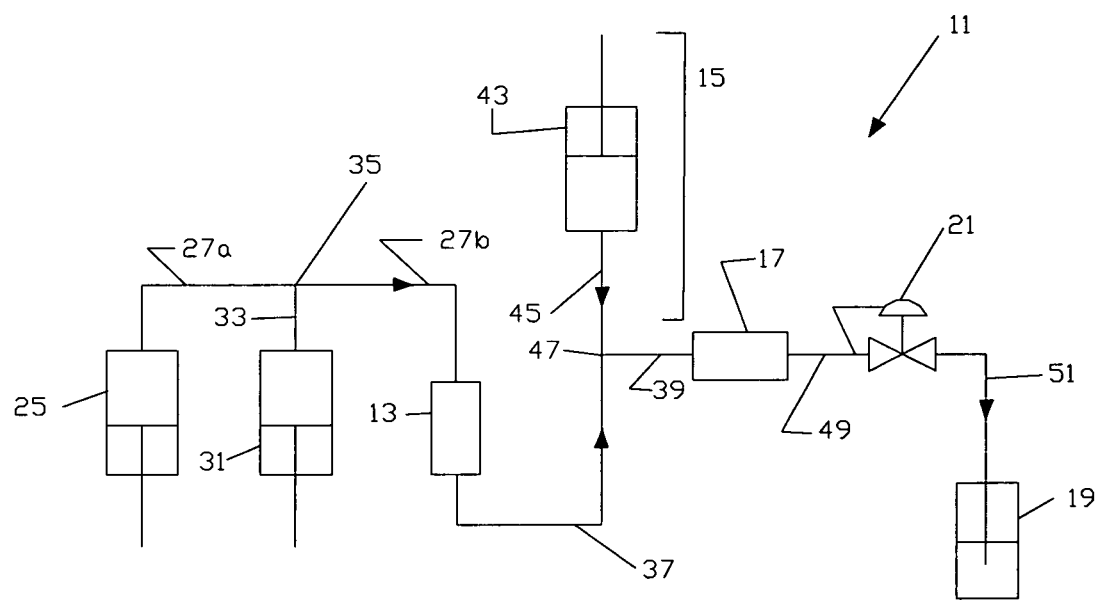

USE OF GINGEROLS FOR CANCER PATIENTS SUFFERING FROM NAUSEA AND EMESIS INDUCED BY CHEMOTHERAPY

GOVERNMENT SUPPORT

Research leading to this invention was in part funded by the National Cancer Institute, National Institutes of Health, Bethesda, Md., USA.

FIELD OF THE INVENTION

This invention relates to methods for making and using gingerols for treating nausea and emesis associated with cancer chemotherapy. The methods feature supercritical, critical and near-critical fluids with and without polar cosolvents.

BACKGROUND OF THE INVENTION

Despite the widespread use of the 5-$HT_3$ receptor antagonist antiemetics, ondansetron (Zofran®, Glaxo Wellcome Oncology/HIV, Research Triangle Park, N.C.) in 1991, granistron (Kytril,® SmithKline Beecham Pharmaceuticals, Philadelphia, Pa.) in 1994, and dolasetron mesylate (Anzemet,® Hoechst Marion Roussel, Kansas City, Mo.), post-chemotherapy nausea and vomiting continue to be reported by up to 70% of patients receiving highly emetogenic chemotherapy agents, such as cisplatin, carboplatin and doxorubicin. Research also suggests that the 5-$HT_3$ receptor antagonists are clinically more effective against emesis than they are against nausea.

Delayed post-chemotherapy nausea is a particularly difficult problem as it does not develop until after the patient has left the treatment location and is not well-controlled by currently available antiemetics. Data from a recently completed URCC CCOP Research Base study of patients receiving cisplatin, carboplatin or doxorubicin indicates that although nausea from receipt of these drugs is most likely to develop within the first 48 hours after administration of chemotherapy, in 18% of the patients it was first reported on or after Day 3 of the cycle.

Patients who suffer from post-chemotherapy nausea may also develop symptoms in anticipation of treatment. Anticipatory nausea (AN) is reported by approximately 20% of patients at any one chemotherapy cycle and by 25-30% of patients by the fourth chemotherapy cycle. Anticipatory vomiting (AV) develops in 8-20% of patients. No pharmacologic agents have had success in treating AN once it has occurred, and, although the behavioral method of systematic desensitization can be effective, it is not readily available in most clinic settings.

All in all, there is still a great deal of room for improvement in the control of nausea and vomiting (NV) associated with chemotherapy for cancer. Furthermore, antiemetics currently in widespread use have been associated with significant adverse effects, such as sedation, extra-pyramidal side effects and hypotension (associated with dopamine antagonists), as well as headache, diarrhea or constipation (associated with 5-$HT_3$ receptor antagonists). A desirable attribute in any substitute or additional antiemetic medication would be the absence of clinically significant adverse effects.

SUMMARY OF THE INVENTION

Embodiments of the present invention are directed to compositions of matter, formulations for the treatment of nausea in humans and animals, methods of treatment, and methods of making such compositions and formulations. One embodiment of the present invention directed to a composition of matter is an extract of the ginger rhizome. The extract has 6-gingerol, 8-gingerol, 10-gingerol, and 6-shogaol, in which 6-shogaol and 6-gingerol define a ratio and the ratio of 6-shogaol to 6-gingerol is 0.04 to 0.40. Although the applicant does not wish to be bound to any theory, it is believed this ratio of 6-shogaol to 6-gingerol improves the efficacy of the extract for the treatment of nausea.

As a further aspect of the invention, one composition of matter is directed to an extract of ginger rhizome wherein the ginger rhizome has a starting mass and the extract has a mass associated with one or more of the following 6-gingerol, 8-gingerol, 10-gingerol, and 6-shogaol. The ratio of 6-gingerol, 8-gingerol, 10-gingerol, and 6-shogaol total mass to starting mass is 20-40%.

As a further aspect of the invention, one composition of matter is directed to an extract having 15-25% 6-gingerol, 1-5% 8-gingerol, 1-5% 10-gingerol and 1-5% 6-shogaol.

A further aspect of the present invention is directed to a formulation. As used herein the term formulation refers to a drug delivery device in the nature of a solution, tablet, capsule, gelcap, suspension and the like having a drug carried within for administration to an animal or human. One formulation of the present invention is directed to an extract of ginger rhizome, for the treatment of nausea in animals and humans, in an oil base.

In one aspect, the formulation the oil base is held in a capsule or gelcap. The capsule or gelcap has an oil base held in the capsule or gelcap.

The formulation has a dosage and in one aspect the dosage is in a range of 20-40 mg of the extract of ginger rhizome. This amount of extract preferably has 4.00-14 mg of combined gingerols and shogaol.

A preferred formulation has an oil with an antioxidant, that is, the antioxidant is dissolved in or suspended in the oil. One antioxidant is tocopherol. A preferred formulation has an oil having one or more emulsifying agents. The emulsifying agents facilitate bioavailability and maintain the other components of the formulation in the oil base. A preferred emulsifying agent is selected from one or more of the following agents lecithin, and short chain, medium chain and long chain triglycerides. A preferred oil is olive oil.

A further aspect of the present invention is a method of treating nausea in humans. The method comprising administering an effective amount of any extract described above or any formulations described above.

Preferably, the effective amount is administered every three to four hours. The method is of particular utility for cancer patients suffering from nausea and emesis induced by chemotherapy.

A further aspect of the present invention is directed to a method of making any of the compositions described above. The method comprises the steps of forming a dried powdered biomass of ginger rhizome. This dried biomass is placed in a vessel with carbon dioxide under super critical, near critical or critical conditions to form a saturated biomass powder. The carbon dioxide is separate from said biomass to form a carbon dioxide fluid extract containing the composition of gingerols and shogaol.

Preferably, the carbon dioxide is held at a temperature of 20-50 degrees Celsius, at a pressure of 1000 to 4000 psi. Preferably, the carbon dioxide has a modifier, in the sense that the modifier is carried in the carbon dioxide in the nature of a dissolved constituent. A preferred modifier is an alcohol, such as methanol or ethanol.

These and other features and advantages will be apparent to those skilled in the art upon reading the detailed description and viewing the drawings briefly described below.

BRIEF DESCRIPTION OF THE DRAWINGS

FIG. 1 depicts in schematic form an apparatus embodying features of the present invention;

DETAILED DESCRIPTION OF PREFERRED EMBODIMENTS

Ginger, an ancient spice mentioned in both the Bible and the Koran, is most known for its role as a flavoring agent for food in Asian and Indian recipes. Since the 16$^{th}$ century, the dried aromatic rhizome (underground stem) of ginger (*Zingiber Officinale*, Roscoe), has also been used by practitioners of both Indian (Ayurvedic) and traditional Chinese medicine to treat gastrointestinal upsets such as nausea and excessive flatulence. North American folklore also recognizes the ability of ginger to relieve gastrointestinal upsets including nausea. Ginger is also believed to be the only herb that can prevent symptoms of motion sickness and it has been approved for that use by Germany's Commission E, the agency responsible for regulating the use of herbal products in that country. Recently ginger has been studied scientifically for its effect on nausea and vomiting associated with motion sickness, surgery and pregnancy.

In an early randomized trial, ginger was more effective than diphenhydramine (Dramamine®) and each was more effective than dried chickweed herb placebo in preventing gastrointestinal symptoms caused by vection-induced motion sickness in a study of college students with self-reported high susceptibility to motion sickness. Ginger was also more effective than placebo in reducing vomiting related to seasickness in a group of naval cadets. Fewer episodes of nausea were also reported by the 40 cadets who received the ginger although the difference was not statistically significant. When used to prevent motion sickness, it is frequently suggested that the ginger be started one to two days before the trip and be continued throughout the period of travel.

A number of published studies have addressed the use of ginger for prevention of post-operative nausea and vomiting although the results have been mixed. Two studies comparing ginger (0.5 gm or 1 gm) vs. metochlopramide (10 mg) vs. placebo for control of post-operative nausea in women undergoing gynecologic surgery demonstrated equal effectiveness of ginger and metochlopramide for post-operative nausea; in both studies ginger and metochlopramide were significantly more effective than placebo. Phillips and co-investigators reported no significant differences in frequency of emesis between the three arms while Bone and colleagues reported less vomiting for both active drugs than for placebo. In the study headed by Phillips participants assigned to the ginger arm required significantly less post-operative "rescue" antiemetic treatment.

Two other studies of post-operative nausea and vomiting found no significant effect of ginger. In one of these, 0.5 gm or 1.0 gm of ginger given pre-operatively had no greater effect than placebo on the frequency or severity of nausea or the frequency of vomiting. Outcomes were assessed three hours post-operatively. However, no standard antiemetic arm was included in the study design. Visalyaputra and colleagues compared 2.0 gm of oral ginger, 1.25 mg intravenous droperidol and placebo in a randomized fashion and reported no differences in the frequency or severity of post-operative nausea or the frequency of post-operative vomiting during the 24 hour period immediately following surgery. Potential confounding factors in studies of post-operative nausea and vomiting include the nausea inducing effect of agents used to induce and maintain anesthesia and provide pain relief and short assessment periods, allowing little time for ginger to exert its maximum anti-nausea effects.

A recent study of ginger for nausea and vomiting of pregnancy found a significant reduction of nausea over four days of treatment in women who were experiencing either nausea or vomiting. Sixty women were randomized in equal proportions to receive 250 mg of dried ginger or placebo in identical-appearing capsules four times daily for four days (a total of 1 gm of ginger each day). By the fourth day, nausea scores were significantly lower in the group of 32 women taking ginger than in the 35 women in the placebo arm. In an earlier randomized, controlled cross-over study, thirty women with hyperemesis gravidarum also reported that ginger was more effective than placebo over a four-day period.

Remarkably little published work has addressed the efficacy of ginger for prevention or treatment of nausea and vomiting caused by receipt of chemotherapy for cancer, and those studies that are available are plagued by design inadequacies including small sample sizes and non-validated assessment methods. In a published nursing doctoral dissertation, Pace studied 20 patients being treated for leukemia with cytosine arabinoside (ARA-C). Participants were given 10 mg intravenous Compazine® (prochlorperazine) prior to chemotherapy and every four hours for nine additional doses. They were also randomly assigned to receive either ginger capsules (0.5 g prior to chemotherapy followed by nine additional doses four hours apart) or an identical-appearing placebo on the same schedule. Participants who received ginger had significantly less severe nausea on the day of chemotherapy and on the following day than those taking the placebo capsules. Another study compared ginger (1.5 gm) to psoralen in patients receiving 8-MOP for extra-corporeal chemotherapy and found that the total nausea score was reduced by approximately one-third in those receiving ginger. Table 1 on the following page summarizes the results of previously conducted controlled studies of ginger for nausea.

TABLE 1

Studies Examining the Antiemetic Efficacy of Ginger.

| References | Sample | Study design | Treatment | Results |
| --- | --- | --- | --- | --- |
| Grontved, et al. (1988) | N = 80 cadets | Two-arm, randomized, placebo-controlled trial for control of seasickness. | 1.0 g ginger powder or placebo given once | Ginger was more effective than placebo in controlling vomiting and cold sweats, P < .05, but not for vertigo or nausea. |
| Fischer-Ramussen, et al. (1991) | N = 60 Pregnant women with severe nausea | Placebo-controlled, randomized, crossover study with 2-day washout, for nausea and vomiting associated with morning sickness. | 250 mg dried ginger capsules or placebo 4 x daily for 4 days | Greater relief with ginger than placebo, P < .05. |

TABLE 1-continued

Studies Examining the Antiemetic Efficacy of Ginger.

| References | Sample | Study design | Treatment | Results |
|---|---|---|---|---|
| Bone, et al. (1990) | N = 60 Women undergoing gynecological surgery | Three-arm, randomized, placebo controlled trial of ginger and metochlopramide for control of post-operative nausea and vomiting. Study medication was given orally prior to surgery. | Arm 1 = 1.0 g ginger Arm 2 = 10 mg metochlopramide Arm 3 = placebo | Ginger was more effective than placebo, P < .05 and similar in effectiveness to metochlopramide for nausea and vomiting control. |
| Pace 1986) | N = 41 Patients receiving chemotherapy | Two-arm, randomized, placebo controlled trial of Compazine ®, with or without ginger for control of chemotherapy-induced nausea and vomiting. | 500 mg ginger or placebo prior to treatment and every four hours following treatment for 36 hours | Patients receiving ginger had less nausea than those receiving placebo. |
| Phillips, et al. (1993) | N = 120 women after lapara-scopic gynaecological surgery | 3 parallel arms, placebo controlled, either given metochlopramide or ginger for post operative vomiting and nausea | Arm 1 = 1 gram of ginger powder given one hour prior to anaesthesia Arm 2 = metochlopramide one hour prior to anaesthesia | Less patients need antiemetics afterward with ginger, less likely to be nauseated. 21% nauseated with ginger, 41% with placebo, 27% metochlopramide |
| Arfeen, et al. (1995) | N = 108 women after lapara-scopic gynaecological surgery | 3 parallel arms, placebo controlled, given placebo or one of two doses of ginger for reduction of post surgical nausea and vomiting | Arm 1 = 0.5 g ginger 1 hour prior to surgery and 2 doses after Arm 2 = 1.0 g ginger prior to surgery and 2 doses after Arm 3 = placebo | The ginger did not appear to have a statistically significant effect on the amount of nausea or vomiting post surgery |
| Visalyaputra et al. (1998) | N = 120 women after lapara-scopic gynaecological surgery | 4 parallel arms, placebo controlled received either ginger or 1.25 mg droperidol, or both to reduce post surgical nausea and vomiting | Arm 1 = 1.0 g ginger presurgically Arm 2 = 1.0 g ginger and 1.25 droperidol Arm 3 = 1.25 mg droperidol Arm 4 = placebo | Neither drug showed a statistically significant decrease in nausea or vomiting |
| Meyer & Schwartz, et al. (1995) | N = 11 patients undergoing 8-MOP treatments | Single arm given psoralen at 0.5-0.6 mg/kg prior to treatment, then evaluated, next treatment given ginger and evaluated | 3 capsules of 530 mg each administered 30 min prior to 8-MOP treatment | Those taking the ginger reduced nausea by ⅓ degree of level without ginger |
| Mowrey & Clayson (1982) | N = 36 paid college students with self-rated high susceptibility to motion sickness | 3 arm-randomized, placebo controlled, for vection induced motion sickness ginger versus placebo versus Dramamine ® | Arm 1 = 100 mg Dramamine ® Arm 2 = 940 mg ginger root Arm 3 = placebo given 25-30 minutes prior to test | Ginger was found to be more effective at reducing vection induced motion sickness than placebo as measured by time in induced motion. P < .001 |
| Vutyavanich et al. (2001) | N = 70 pregnant women at or prior to 17 weeks gestation | 2 arm, placebo controlled, double-masked, randomized ginger versus placebo, participants self reported nausea, vomiting, and severity. Lasted four days, and pre/post evaluation of symptoms | Arm 1 = 1.0 g ginger for four days Arm 2 = placebo | Visual analog scores decreased with ginger p = .014, vomiting episodes decrease with p < .001 And the improvement of those in ginger group with p < .001 |

Previous research suggests that ginger may be effective against nausea associated with chemotherapy, but design inadequacies and small numbers limit the power and generalizability of the results and no dose-response studies have been reported to date. A phase II/III randomized, dose-finding, placebo-controlled clinical trial was conducted to assess the efficacy of ginger (Zingiber Officinale) for nausea associated with chemotherapy for cancer in the CCOP member sites affiliated with the URCC CCOP Research Base. Innovative aspects of the study design include collecting baseline data on nausea following the second cycle of chemotherapy, beginning the intervention three days prior to chemotherapy to maximize the post-chemotherapy effect of ginger, assessing symptoms prior to taking any ginger, after three days of ginger alone, and after three days of ginger plus standard antiemetics at cycles three and four, assessing anticipatory nausea as well as acute and delayed post-chemotherapy nausea and using validated measures for outcome assessment. The primary outcome was assessment of nausea following one chemotherapy cycle with the intervention (the third cycle). The intervention was continued for the fourth cycle of chemotherapy to assess the consistency of any effectiveness of ginger for nausea as a secondary, exploratory analysis.

In the largest trial to date, Ryan et al. (2009) conducted a Phase II/III randomized, placebo-controlled, double-blind clinical trial to assess the efficacy of ginger for chemotherapy-induced nausea in cancer patients. Patients who had experienced nausea in a previous chemotherapy cycle were randomized into four arms: (1) placebo, (2) 0.5 g ginger; (3) 1.0 g ginger, or (4) 1.5 g ginger. All patients received 5-HT$_3$ receptor antagonist anti-emetics on Day 1 of all cycles and took ginger or placebo twice daily for six days starting three days before the first day of the next two cycles. 644 patients with disparate cancer types were accrued (90% female, mean age=53). All doses of ginger significantly reduced nausea on Day 1 of cycles 2 and 3 (p=0.003). The largest reduction in nausea occurred with 0.5 g and 1.0 g of ginger. Time of day had a significant effect on nausea (p<0.001) with a linear decrease over 24 hours for patients using ginger. No significant adverse events were reported. This positive trial utilized a ginger product in a gel capsule with the concentrations of gingerols and shogaol in the Examples herein.

Aspects of the present invention employ materials known as supercritical, critical or near-critical fluids. A material becomes a critical fluid at conditions which equal its critical temperature and critical pressure. A material becomes a supercritical fluid at conditions which equal or exceed both its critical temperature and critical pressure. The parameters of critical temperature and critical pressure are intrinsic thermodynamic properties of all sufficiently stable pure compounds and mixtures. Carbon dioxide, for example, becomes a supercritical fluid at conditions which equal or exceed its critical temperature of 31.1° C. and its critical pressure of 72.8 atm (1,070 psig). In the supercritical fluid region, normally gaseous substances such as carbon dioxide become dense phase fluids which have been observed to exhibit greatly enhanced solvating power. At a pressure of 3,000 psig (204 atm) and a temperature of 40° C., carbon dioxide has a density of approximately 0.8 g/cc and behaves much like a nonpolar organic solvent, having a dipole moment of zero Debyes.

A supercritical fluid displays a wide spectrum of solvation power as its density is strongly dependent upon temperature and pressure. Temperature changes of tens of degrees or pressure changes by tens of atmospheres can change a compound solubility in a supercritical fluid by an order of magnitude or more. This feature allows for the fine-tuning of solvation power and the fractionation of mixed solutes. The selectivity of nonpolar supercritical fluid solvents can also be enhanced by addition of compounds known as modifiers (also referred to as entrainers or cosolvents). These modifiers are typically somewhat polar organic solvents such as acetone, ethanol, methanol, methylene chloride or ethyl acetate. Varying the proportion of modifier allows wide latitude in the variation of solvent power.

In addition to their unique solubilization characteristics, supercritical fluids possess other physicochemical properties which add to their attractiveness as solvents. They can exhibit liquid-like density yet still retain gas-like properties of high diffusivity and low viscosity. The latter increases mass transfer rates, significantly reducing processing times. Additionally, the ultra-low surface tension of supercritical fluids allows facile penetration into microporous materials, increasing extraction efficiency and overall yields.

A material at conditions that border its supercritical state will have properties that are similar to those of the substance in the supercritical state. These so-called "near-critical" fluids are also useful for the practice of this invention. For the purposes of this invention, a near-critical fluid is defined as a fluid which is (a) at a temperature between its critical temperature ($T_c$) and 75% of its critical temperature and at a pressure at least 75% of its critical pressure, or (b) at a pressure between its critical pressure ($P_c$) and 75% of its critical pressure and at a temperature at least 75% of its critical temperature. In this definition, pressure and temperature are defined on absolute scales, e.g., Kelvin and psia. To simplify the terminology, materials which are utilized under conditions which are supercritical, near-critical or exactly at their critical point will jointly be referred to as "SCCNC" fluids or referred to as "SFS."

SCCNC fluids can be used for the fractional extraction and manufacturing of highly purified gingerols and shogaols.

Embodiments of the present invention are directed to methods of using supercritical fluids for isolating and manufacturing gingerols for use as a therapeutic to treat nausea and emesis.

The present method and apparatus will be described with respect to FIG. 1 which depicts in schematic form the ginger fractionation apparatus, generally designated by the numeral 11.

Polarity-guided SuperFluids™ fractionation can be carried out on the dried and fresh ginger powder. SuperFluids™ CXF fractionations can be carried out on an automated extractor or a manual version of the same. As shown in FIG. 1, this is a dual pump system, utilizing syringe pump 1 for neat critical fluid (e.g. $CO_2$) and syringe pump 2 for modifier (e.g. ethanol).

After loading ginger into a cartridge on the cartridge holder 3, the fractionation procedure can start. For example, the system will be brought to 3,000 psig and 40° C., and extracted for 10 minutes with pure CO2. This fraction will be collected in ethanol in a glass vial, numbered 4 in FIG. 1. The extraction parameters will be then set to: Supercritical CO2 at 3,000 psig and extraction temperature 40° C., step extractions with ethanol as cosolvent at 5, 10, 20, 30 and 40 vol % each step being 10 min. Each biomass sample will yield 6 fractions and which will be collected in ethanol in separate glass vials. The fractions will be dried under vacuum in a SpeedVac, and analyzed by HPLC for gingerols, zingerone, and shogaol content. Conditions which provide the highest combined content of gingerols and shogaol with ratios of 6-gingerol to 6-shogaol between 0.04 to 0.4 will be scaled up for manufacturing larger quantities.

EXAMPLES

Example 1

Fractionation of Ginger Rhizome

Biomass: *Zingiber officinale* biomass, both fresh and dried, was obtained from reputable suppliers in Brazil. The material was shipped on ice by overnight freight to our facilities in Woburn, Mass. On receipt, the biomass samples were logged in; dried biomass was stored in dry, low humidity conditions and the fresh biomass will be stored at 4° C. Samples were ground to a fine powder and extracted with different solvents—ethanol, methylene chloride, chloroform and hexane—to define the gingerol content of the material by HPLC analytical techniques. Samples of the underground biomass were used for cultivar identification and sent to outside contractors for heavy metals, herbicides and pesticides analyses. Small voucher samples were retained.

Ginger Powder: The dried ginger root was cut into chunks and dried in a convective oven at 37° C. for 24 hours to remove moisture. The biomass was then ground into a fine powder in a plate and hammer mill. A sample of this fine powder was also extracted by conventional techniques to re-establish the gingerols and shogaol content of the dried and ground *Zingiber officinale* biomass. The biomass powder was labeled and stored at −20° C.

The fresh ginger root was also cut into chunks and dried in a VirTis shelf freeze-dryer over a 24-hour period to remove all water and moisture. The biomass was then ground into a fine powder in a plate and hammer mill. A sample of this fine powder was also extracted by conventional techniques to re-establish the gingerols and shogaol content of the dried and ground *Zingiber officinale* biomass. The biomass powder was labeled and stored at −20° C.

Ginger Extract: Polarity-guided SuperFluids™ fractionation was carried out on the dried and fresh ginger powder. As shown in FIG. 1, this is a dual pump system, utilizing syringe pump 1 for neat critical fluid (e.g. $CO_2$) and syringe pump 2 for modifier (e.g. ethanol).

Example 1

Fractionation of Ginger Rhizome

| | SC-CO2 Extraction Parameters | | | Biomass | | | % Gingerol In Extracted Material | | | | 6-Shogaol | | Total % |
|---|---|---|---|---|---|---|---|---|---|---|---|---|---|
| Fraction ID | P, psig | ToC | % EtOH | Starting Wt., g | Wt. of Extracted Material, mg | % Extracted | 6-Gingerol | 8-Gingerol | 10-Gingerol | Total | % in Extracted Material | Ratio of 6-Shogaol to 6-Gingerol | Gingerols plus Shogaol in Extract |
| GIN-1-1 | 3000 | 40 | 0 | 1.9960 | 6.00 | 0.30% | 5.89% | 0.93% | 0.017% | 6.84% | 4.45% | 0.76 | 11.30% |
| GIN-1-2 | 3000 | 40 | 5 | 1.9960 | 3.10 | 0.16% | 5.10% | 0.72% | 0.029% | 5.85% | 3.73% | 0.73 | 9.58% |
| GIN-1-3 | 3000 | 40 | 10 | 1.9960 | 32.90 | 1.65% | 18.42% | 3.08% | 0.161% | 21.66% | 13.59% | 0.74 | 35.26% |
| GIN-1-4 | 3000 | 40 | 15 | 1.9960 | 29.60 | 1.48% | 12.17% | 1.91% | 0.119% | 14.21% | 8.13% | 0.67 | 22.34% |
| GIN-1-5 | 3000 | 40 | 20 | 1.9960 | 24.00 | 1.20% | 3.09% | 0.41% | 0.019% | 3.52% | 1.74% | 0.56 | 5.25% |
| GIN-1-6A | 3000 | 40 | 40 | 1.9960 | 9.60 | 0.48% | 1.45% | 0.08% | 0.014% | 1.55% | 0.58% | 0.40 | 2.13% |
| GIN-1-6B | 3000 | 40 | 40 | 1.9960 | 20.30 | 1.02% | 0.86% | 0.07% | 0.010% | 0.94% | 0.30% | 0.35 | 1.24% |
| GIN-2-1 | 1000 | 40 | 0 | 2.1253 | 23.43 | 1.10% | 0.06% | 0.01% | 0.000% | 0.07% | 0.027% | 0.42 | 0.10% |
| GIN-2-2 | 1000 | 40 | 5 | 2.1253 | 21.12 | 0.99% | 0.05% | 0.00% | 0.000% | 0.06% | 0.004% | 0.08 | 0.06% |
| GIN-2-3 | 1000 | 40 | 10 | 2.1253 | 45.17 | 2.13% | 11.20% | 2.33% | 0.162% | 13.69% | 9.75% | 0.87 | 23.44% |
| GIN-2-4 | 1000 | 40 | 15 | 2.1253 | 47.11 | 2.22% | 3.09% | 0.52% | 0.022% | 3.63% | 2.42% | 0.79 | 6.05% |
| GIN-2-5 | 1000 | 40 | 20 | 2.1253 | 67.14 | 3.16% | 0.49% | 0.06% | 0.004% | 0.56% | 0.32% | 0.65 | 0.88% |
| GIN-2-6A | 1000 | 40 | 40 | 2.1253 | 30.00 | 1.41% | 0.36% | 0.01% | 0.002% | 0.37% | 0.14% | 0.38 | 0.50% |
| GIN-2-6B | 1000 | 40 | 40 | 2.1253 | 22.41 | 1.05% | 0.38% | 0.01% | 0.002% | 0.40% | 0.13% | 0.35 | 0.53% |
| GIN-3-1 | 5000 | 40 | 0 | 2.1146 | 1.35 | 0.06% | 19.54% | 2.99% | 0.069% | 22.60% | 12.60% | 0.64 | 35.20% |
| GIN-3-2 | 5000 | 40 | 5 | 2.1146 | 0.55 | 0.03% | 17.59% | 2.12% | 0.163% | 19.87% | 10.40% | 0.59 | 30.28% |
| GIN-3-3 | 5000 | 40 | 10 | 2.1146 | 48.36 | 2.29% | 15.78% | 2.84% | 0.162% | 18.78% | 12.68% | 0.80 | 31.46% |
| GIN-3-4 | 5000 | 40 | 15 | 2.1146 | 15.06 | 0.71% | 8.16% | 1.31% | 0.056% | 9.52% | 5.94% | 0.73 | 15.45% |
| GIN-3-5 | 5000 | 40 | 20 | 2.1146 | 10.62 | 0.50% | 3.42% | 0.38% | 0.035% | 3.84% | 1.79% | 0.52 | 5.63% |
| GIN-3-6A | 5000 | 40 | 40 | 2.1146 | 8.00 | 0.38% | 1.78% | 0.16% | 0.023% | 1.97% | 0.79% | 0.44 | 2.76% |
| GIN-3-6B | 5000 | 40 | 40 | 2.1146 | 7.10 | 0.34% | 2.11% | 0.20% | 0.025% | 2.33% | 0.91% | 0.43 | 3.24% |
| GIN-4-1 | 4000 | 40 | 0 | 2.0110 | 46.06 | 2.29% | 16.62% | 2.85% | 0.145% | 19.62% | 13.01% | 0.78 | 32.63% |
| GIN-5-1 | 2000 | 40 | 0 | 2.0522 | 57.95 | 2.82% | 20.23% | 3.51% | 0.223% | 23.97% | 15.32% | 0.76 | 39.29% |
| GIN-6-1 | 3000 | 30 | 0 | 2.0086 | 19.44 | 0.97% | 14.14% | 2.45% | 0.135% | 16.73% | 11.28% | 0.80 | 28.01% |
| GIN-7-1 | 3000 | 21 | 0 | 2.0382 | 35.52 | 1.74% | 19.30% | 3.37% | 0.152% | 22.82% | 15.49% | 0.80 | 38.30% |
| GIN-8-1 | 3000 | 50 | 0 | 2.0683 | 42.68 | 2.06% | 18.28% | 3.09% | 0.149% | 21.52% | 14.21% | 0.78 | 35.72% |
| GIN-9-1 | 3000 | 60 | 0 | 2.0223 | 48.30 | 2.39% | 21.94% | 3.76% | 0.169% | 25.87% | 16.94% | 0.77 | 42.81% |
| GIN-10-1 | 3000 | 40 | 0 | 2.0552 | 57.78 | 2.81% | 13.77% | 2.36% | 0.123% | 16.25% | 11.07% | 0.80 | 27.33% |
| GIN-11-1 | 1000 | 40 | 0 | 2.0100 | 108.21 | 5.38% | 0.25% | 0.04% | 0.002% | 0.29% | 0.20% | 0.80 | 0.49% |
| GIN-12-1 | 5000 | 40 | 0 | 2.0046 | 55.30 | 2.76% | 20.53% | 3.50% | 0.200% | 24.23% | 15.95% | 0.78 | 40.17% |
| Ethanol | 0 | <40 | 100 | 2.0208 | 173.50 | 8.59% | 7.46% | 1.21% | 0.039% | 8.71% | 5.58% | 0.75 | 14.28% |

Example 2

Fractionation of Ginger Rhizome

| | Biomass | | | % Gingerol in Extracted Material | | | | 6-Shogaol | | Total % |
|---|---|---|---|---|---|---|---|---|---|---|
| Sample | Starting Wt., g | Wt. of Extracted Material, g | % Extracted | 6-Gingerol | 8-Gingerol | 10-Gingerol | Total | % in Extracted Material | Ratio of 6-Shogaol to 6-Gingerol | Gingerols plus Shogaol |
| GINP-1-1 | 8618 | 124.3 | 1.44 | 20.05 | 2.083 | 3.065 | 25.20 | 1.88 | 0.09 | 27.08 |
| GINP-1-2 | 8618 | 33.6 | 0.39 | 25.79 | 2.936 | 5.268 | 34.00 | 1.19 | 0.05 | 35.19 |
| GINP-1-3 | 8618 | 26.9 | 0.31 | 20.43 | 2.433 | 4.893 | 27.75 | 0.55 | 0.03 | 28.30 |
| GINP-1-4 | 8618 | 21.0 | 0.24 | 17.15 | 1.952 | 3.931 | 23.03 | 0.53 | 0.03 | 23.56 |
| GINP-1-5 | 8618 | 12.9 | 0.15 | 15.36 | 1.777 | 3.592 | 20.73 | 0.46 | 0.03 | 21.19 |
| GINP-1-6 | 8618 | 15.0 | 0.17 | 17.34 | 2.087 | 4.301 | 23.73 | 0.47 | 0.03 | 24.21 |
| Total | 8618 | 233.7 | 2.71 | 20.22 | 2.218 | 3.778 | 26.22 | 1.34 | 0.07 | 27.56 |

Example 3

Fractionation of Ginger Rhizome

| | Biomass | | | | | | | 6-Shogaol | | |
|---|---|---|---|---|---|---|---|---|---|---|
| | Starting | Wt. of Extracted | % | % Gingerol In Extracted Material | | | | % in Extracted | Ratio of 6-Shogaol to | Total % Gingerols |
| Sample | Wt., g | Material, g | Extracted | 6-Gingerol | 8-Gingerol | 10-Gingerol | Total | Material | 6-Gingerol | plus Shogaol |
| GINP-2-1 | 9752 | 87.0 | 0.89 | 12.60 | 1.217 | 1.780 | 15.60 | 1.60 | 0.13 | 17.20 |
| GINP-2-2 | 9752 | 63.8 | 0.65 | 27.33 | 3.096 | 4.770 | 35.19 | 2.07 | 0.08 | 37.26 |
| GINP-2-3 | 9752 | 39.0 | 0.40 | 28.27 | 3.325 | 5.741 | 37.34 | 1.59 | 0.06 | 38.92 |
| GINP-2-4 | 9752 | 36.9 | 0.38 | 25.50 | 3.297 | 5.933 | 34.73 | 1.30 | 0.05 | 36.03 |
| GINP-2-5 | 9752 | 42.3 | 0.43 | 24.56 | 2.940 | 5.725 | 33.23 | 0.94 | 0.04 | 34.16 |
| Total | 9752 | 269.0 | 2.76 | 22.02 | 2.524 | 4.254 | 28.79 | 1.56 | 0.07 | 30.36 |

Example 4

Fractionation of Ginger Rhizome

Although the SFS-$CO_2$ extraction parameters of T=40° C., 2,000 psig and no co-solvent were the same for the three series, the $CO_2$ flow rate was reduced from GINP-1 to GINP-2. Additionally, collection techniques from GINP-2 to GINP-3 were changed.

| | Biomass | | | | | | | 6-Shogaol | | Total % Gingerols |
|---|---|---|---|---|---|---|---|---|---|---|
| | Starting | Wt. of Extracted | % | % Gingerol In Extracted Material | | | | % in Extracted | Ratio of 6-Shogaol to | plus Shogaol in the Extracted |
| Sample | Wt., g | Material, g | Extracted | 6-Gingerol | 8-Gingerol | 10-Gingerol | Total | Material | 6-Gingerol | Material |
| GINP-3-1 | 9072 | 178.8 | 1.97 | 18.32 | 1.823 | 2.677 | 22.82 | 1.86 | 0.10 | 24.68 |
| GINP-3-2 | 9072 | 88.8 | 0.98 | 25.38 | 2.876 | 4.740 | 32.99 | 1.82 | 0.07 | 34.81 |
| GINP-3-3 | 9072 | 46.9 | 0.52 | 24.25 | 2.813 | 5.036 | 32.09 | 1.43 | 0.06 | 33.52 |
| GINP-3-4 | 9072 | 24.0 | 0.26 | 20.36 | 2.111 | 3.861 | 26.34 | 0.69 | 0.03 | 27.03 |
| Total | 9072 | 338.4 | 3.73 | 21.14 | 2.257 | 3.629 | 27.02 | 1.70 | 0.08 | 28.73 |

Example 5

Fractionation of Ginger Rhizome

| | Biomass | | | | | | | 6-Shogaol | | |
|---|---|---|---|---|---|---|---|---|---|---|
| | Starting | Wt. of Extracted | % | % Gingerol in Extracted Material | | | | % in Extracted | Ratio of 6-Shogaol to | Total % Gingerols |
| Sample | Wt., g | Material, g | Extracted | 6-Gingerol | 8-Gingerol | 10-Gingerol | Total | Material | 6-Gingerol | plus Shogaol |
| GINP-5-1 | 8845 | 148.1 | 1.67 | 16.09 | 1.460 | 2.110 | 19.66 | 1.80 | 0.112 | 21.46 |
| GINP-5-2 | 8845 | 52.6 | 0.59 | 35.65 | 3.949 | 5.780 | 45.38 | 1.57 | 0.044 | 46.95 |
| GINP-5-3 | 8845 | 35.9 | 0.41 | 33.14 | 3.968 | 8.238 | 45.35 | 0.91 | 0.028 | 46.26 |
| GINP-5-4 | 8845 | 14.3 | 0.16 | 30.69 | 3.908 | 7.675 | 42.27 | 0.54 | 0.018 | 42.81 |
| GINP-5-5 | 8845 | 13.7 | 0.15 | 24.98 | 3.686 | 7.364 | 36.03 | 0.37 | 0.015 | 36.40 |
| GINP-5-6 | 8845 | 7.1 | 0.08 | 18.22 | 2.746 | 6.004 | 26.97 | 0.24 | 0.013 | 27.21 |
| GINP-5-7 | 8845 | 5.3 | 0.06 | 12.94 | 2.023 | 4.784 | 19.75 | 0.24 | 0.018 | 19.98 |
| GINP-5-8 | 8845 | 7.5 | 0.08 | 13.97 | 1.888 | 4.415 | 20.28 | 0.49 | 0.035 | 20.77 |
| Total | 8845 | 284.4 | 3.22 | 22.96 | 2.521 | 4.302 | 29.78 | 1.41 | 0.062 | 31.19 |

Example 6

Fractionation of Ginger Rhizome

The SFS-$CO_2$ extraction parameters were T=40° C., 2,000 psig and no co-solvent. The feed rate of $CO_2$ had a pump rate of 4 strokes/minute MeOH to 80 strokes per minute $CO_2$. Five (5) fractions were collected every 60 minutes.

| | Biomass | | | | | | | 6-Shogaol | | |
|---|---|---|---|---|---|---|---|---|---|---|
| Sample | Starting Wt., g | Wt. of Extracted Material, g | % Extracted | % Gingerol in Extracted Material | | | | % in Extracted Material | Ratio of 6-Shogaol to 6-Gingerol | Total % Gingerols plus Shogaol |
| | | | | 6-Gingerol | 8-Gingerol | 10-Gingerol | Total | | | |
| GINP-6-1 | 8165 | 80.3 | 0.98 | 18.44 | 1.818 | 2.644 | 22.90 | 1.79 | 0.097 | 24.69 |
| GINP-6-2 | 8165 | 83.5 | 1.02 | 27.64 | 3.118 | 5.215 | 35.97 | 1.80 | 0.065 | 37.77 |
| GINP-6-3 | 8165 | 47.0 | 0.58 | 26.17 | 3.263 | 5.995 | 35.43 | 1.34 | 0.051 | 36.77 |
| GINP-6-4 | 8165 | 12.9 | 0.16 | 15.81 | 2.122 | 3.913 | 21.84 | 0.60 | 0.038 | 22.45 |
| GINP-6-5 | 8165 | 2.5 | 0.03 | 10.77 | 1.330 | 2.510 | 14.61 | 0.35 | 0.032 | 14.96 |
| Total | 8165 | 226.2 | 2.77 | 23.21 | 2.610 | 4.360 | 30.18 | 1.61 | 0.070 | 31.79 |

Example 7

Fractionation of Ginger Rhizome

| | Biomass | | | | | | | 6-Shogaol | | |
|---|---|---|---|---|---|---|---|---|---|---|
| Sample | Starting Wt., g | Wt. of Extracted Material, g | % Extracted | % Gingerol in Extracted Material | | | | % in Extracted Material | Ratio of 6-Shogaol to 6-Gingerol | Total % Gingerols plus Shogaol |
| | | | | 6-Gingerol | 8-Gingerol | 10-Gingerol | Total | | | |
| GINP-7-1 | 9866 | 159.9 | 1.62 | 21.70 | 2.051 | 2.893 | 26.65 | 2.34 | 0.108 | 28.98 |
| GINP-7-2 | 9866 | 78.7 | 0.80 | 34.68 | 4.923 | 8.132 | 47.74 | 0.97 | 0.028 | 48.71 |
| GINP-7-3 | 9866 | 25.9 | 0.26 | 18.28 | 2.902 | 6.088 | 27.27 | 0.42 | 0.023 | 27.69 |
| GINP-7-4 | 9866 | 14.3 | 0.14 | 10.94 | 1.516 | 3.351 | 15.81 | 0.32 | 0.029 | 16.12 |
| GINP-7-5 | 9866 | 2.8 | 0.03 | 9.49 | 1.263 | 2.714 | 13.47 | 0.25 | 0.026 | 13.72 |
| Total | 9866 | 281.6 | 2.85 | 24.35 | 2.897 | 4.673 | 31.92 | 1.66 | 0.068 | 33.57 |

Example 8

Fractionation of Ginger Rhizome

| | Biomass | | | | | | | 6-Shogaol | | Total % Gingerols plus Shogaol in the Extracted Material |
|---|---|---|---|---|---|---|---|---|---|---|
| Sample | Starting Wt., g | Wt. of Extracted Material, g | % Extracted | % Gingerol in Extracted Material | | | | % in Extracted Material | Ratio of 6-Shogaol to 6-Gingerol | |
| | | | | 6-Gingerol | 8-Gingerol | 10-Gingerol | Total | | | |
| GINP-8-1 | 9866 | 193.4 | 1.96 | 23.92 | 2.355 | 3.272 | 29.54 | 2.24 | 0.09 | 31.78 |
| GINP-8-2 | 9866 | 66.2 | 0.67 | 26.29 | 4.261 | 8.288 | 38.84 | 0.72 | 0.03 | 39.56 |
| GINP-8-3 | 9866 | 16.4 | 0.17 | 13.37 | 1.856 | 3.415 | 18.64 | 0.49 | 0.04 | 19.13 |
| GINP-8-4 | 9866 | 7.3 | 0.07 | 11.02 | 1.371 | 2.700 | 15.09 | 0.37 | 0.03 | 15.46 |
| Total | 9866 | 283.3 | 2.87 | 23.53 | 2.746 | 4.438 | 30.71 | 1.74 | 0.07 | 32.45 |

Example 9

Fractionation of Ginger Rhizome

| | Biomass | | | Gingerol in Extracted Material | | | | | | Total Gingerols plus Shogaol in the Extracted Material |
|---|---|---|---|---|---|---|---|---|---|---|
| Sample | Starting Biomass Wt., g | Wt. of Lot, g* | % Extracted | 6-Gingerol | 8-Gingerol | 10-Gingerol | Total Gingerols | 6-Shogaol | Ratio of 6-Shogaol to 6-Gingerol | |
| | | | | Reported as grams | | | | | | |
| GINP-1 Lot 022810 | 8618 | 277.0 | 3.21 | 49.76 | 5.77 | 9.83 | 65.4 | 3.72 | 0.075 | 69.08 |
| | | | | Reported as % | | | | | | |
| | | | | 17.96 | 2.08 | 3.55 | 23.59 | 1.34 | 0.075 | 24.94 |

Additionally, 100 grams of the 277.0 g was shipped to Cardinal Health/RP Sherer on Oct. 28, 2002, leaving ~177 g of this Lot in-house.

Example 10

Fractionation of Ginger Rhizome

The yields for the composite GINP were:

| Composite | Yield, g | Removed, g | Remaining, g |
|---|---|---|---|
| GINP-1 | 277 | 200 | 77 |
| GINP-2 | 306 | 1 | 305 |
| GINP-3 | 274 | 1 | 273 |
| GINP-4 | 272 | 1 | 271 |

-continued

| Composite | Yield, g | Removed, g | Remaining, g |
|---|---|---|---|
| GINP-5 | 307 | 1 | 306 |
| GINP-6 | 256 | 1 | 255 |
| GINP-7 | 321 | 1 | 320 |
| GINP-8 | 328 | 1 | 327 |
| TOTAL GINP | | | 2134 |

The 8 composite extracts were warmed to 33° C. in a water bath and then transferred into a 10 L round bottom flask. With the rotavaporator bath set at 30° C., the fractions were combined by slowly rotating the flask such that the extract slid into itself with minimal agitation and incorporation of air. The vacuum was not used since this is mainly a mixing procedure.

After 2 hours the following aliquots were taken:

(1). 1,352 g for capsule manufacture, stored −20° C./N₂ head;

(2). 100 g for in-house QC tests;

(3.) 150 g shipped to Flora Research for specified tests including microbiological Testing (4.) 400 g, weighed, labeled and stored at −20° C. under a nitrogen head.

All the apparatus (rotavaporator, R.B. 10 L flask, shipping bottle, storage bottles, funnel, caps, and watch glass were cleaned by either 70% EtOH or autoclaving or combination of both to minimize bioburden. Personnel took appropriate aseptic processing precautions.

| GINP-021311 | | | | | | |
|---|---|---|---|---|---|---|
| 6-Gingerol | 8-Gingerol | 10-Gingerol | Total Gingerols | 6-shogaol | Ratio of 6-Shogaol to 6-Gingerol | Total Gingerols plus Shogaol in the Extracted Material |
| mg per gram extract | | | | | | |
| 207.84 | 24.97 | 40.01 | 272.8 | 15.00 | 0.072 | 287.82 |
| % Target Compound per gram extract | | | | | | |
| 20.78 | 2.50 | 4.00 | 27.28 | 1.50 | 0.072 | 28.78 |

Example 11

Formulation of Gingerols

The active pharmaceutical ingredients (APIs) are (1): 1,026 grams of GINP-021311 (Lot No. 021311); (2) 326 grams of GINP-021311 (Lot No. 021311); and (3) 400 grams of GINP-021311 (Lot No. 021311) for a total of 1.752 kilograms of ginger product. This product has an absolute purity of 28.78 total gingerols and shogaol (20.78% 6-gingerol, 2.50% 8-gingerol, 4.00% 10-gingerol and 1.50% 6-shogaol). APIs were characterized by HPLC analysis.

The ginger drug capsules contained the following: ginger extract (containing combined gingerols and shogaol); mixed tocopherols as an antioxidant; lecithin as an emulsifier to improve solubility and bioavailability; medium chain triglyceride (MCT) as a co-emulsifier; and olive oil as an excipient with some nutritional value under a nitrogen head to minimize product oxidation.

The placebo capsules contained the following: mixed tocopherols; lecithin; medium chain triglyceride (MCT); and olive oil under a nitrogen head.

What is claimed is:

1. A formulation of an extract of ginger rhizome for the treatment of nausea in humans comprising 20-40 mg of extract of ginger rhizome having 15-25% 6-gingerol, 1-5% 8-gingerol, 1-5% 10-gingerol, and 1-5% 6-shogaol in which said 6-gingerol, 8-gingerol, 10-gingerol, and 6-shogaol comprise 4-14 mg in an oil base held in a capsule or gelcap for oral administration every three to four hours as needed for the treatment of nausea.

2. The formulation of claim 1 wherein said oil has an antioxidant.

3. The formulation of claim 2 wherein said antioxidant is tocopherol.

4. The formulation of claim 1 wherein said oil has one or more emulsifying agents.

5. The formulation of claim 4 wherein at least one of said emulsifying agents are selected from lecithin, and short chain, medium chain and long chain triglycerides.

6. The formulation of claim 1 wherein said oil is olive oil.

7. A method of treating nausea in humans comprising the step of administering an effective amount of the formulation as set forth in any one of claim 4 or 2-6.

8. The method of claim 7 wherein said effective amount is administered every three to four hours.

9. The method of claim 7 wherein said step of administering is (a) initiated three days before the start of chemotherapy; (b) performed on the day of chemotherapy; and (c) performed through three days after the end of chemotherapy.

* * * * *